United States Patent [19]

Persoon et al.

[11] Patent Number: Plant 5,496

[45] Date of Patent: Jun. 18, 1985

[54] CHRYSANTHEMUM PLANT DIANA

[76] Inventors: Margot J. Persoon; Johannes A. Persoon, both of 4998 Foothill Rd., Carpinteria, Calif. 93013

[21] Appl. No.: 495,473

[22] Filed: May 17, 1983

[51] Int. Cl.[3] ..... A01H 5/00

[52] U.S. Cl. ..... Plt./76

[58] Field of Search ..... Plt./76

*Primary Examiner*—James R. Feyrer

*Attorney, Agent, or Firm*—James R. Cypher

[57] ABSTRACT

The present invention relates to a new and distinct cultivar of Chrysanthemum Plant, named Diana, a sport of Dolly, distinguished from its parent, as well as any other variety known to me, by its darker lavender flower color and its increased "rolled" or "spoon shaped" petals. The new cultivar, Diana, is similar to its parent Dolly in all other major aspects.

1 Drawing Figure

BACKGROUND OF THE INVENTION

This invention relates to a new and distinct variety of chrysanthemum plant named DIANA which is a sport of the cultivar Dolly, an unpatented commercial variety.

This sport was discovered and selected by us from a flowering of Dolly in our commercial greenhouses in Carpinteria, Calif. on Oct. 21, 1981 because of its unique darker lavender flower color and slightly increased "rolled" or "spoon-shaped" petals. The distinguishing characteristics which are outstanding in the new cultivar and which distinguish it from its parent are as follows:

1. Darker flower color.
2. 5 to 6% more petals "rolled" or "spooned" in shape.

This dark sprot is similar to Dolly in the following characteristics:

1. Foliage.
2. Size of flower.
3. Herbaceaus plant form with vigorous, upright, branching growth.
4. Flowering response.

Asexual reproduction and flowerings of this new cultivar by cuttings was performed at Carpinteria, Calif. and Fremont, Calif. in commercial greenhouses. The new cultivar was found to retain its distinctive characteristics as listed herein through successive propagations.

BRIEF DESCRIPTION OF THE DRAWINGS

The photo depicting the overall form and appearance of the plant does not illustrate the true color of the blooms. The blooms in this photograph show a subdued pink color and do not illustrate the true violet shade of the new cultiver. It does, however, illustrate the vigorous, upright growth habit and strong straight stems.

The photo showing a close up view of the blooms, does illustrate the true color of the new cultivar.

The parentage of the new chrysanthemum plant is as follows: Sport of unpatented commercial variety, Dolly.

The classification of the new variety is as follows:
p0 Botanical: Chrysanthemum morifolium, Ramat.
Commercial: Standard spray The following detailed botanical description is based on observations of plants grown inside commercial greenhouses at Fremont, Calif., and Carpinteria, Calif.

The height of plant and flower and foliage size established as an average using standard commercial cultural practices and the recommended treatment of long day control as known in the industry: one to two weeks long days before initiation of short days. The data provided, accurately characterizes the sport in question. Color designation and other values stated may deviate slightly from the stated values from flowering to flowering, but the deviations will be within the range expected from varying environmental, seasonal, and cultural conditions. The form of the plant is Herbaceous and it grows in an upright branching manner. The following table compares the new cultivar with its parent Dolly.

TABLE OF COMPARISON

| | New Cultivar (Diana) | Dolly |
|---|---|---|
| PLANT: | | |
| Height | 120 cm | Same |
| Response | 9 weeks | Same |
| Form | Herbacious | Same |
| Growth: | Vigorous, upright, branching | Same |
| Blooming Season: | Year around | Same |
| FOLIAGE: | | |
| Color - Upper side | 136 A | Same |
| Lower side | 138 A | Same |
| Size: | Length 15.25 cm × 8.6 cm width | Same |
| Quantity | Numerous | Same |
| Shape | Obvate lobed | Same |
| Texture | Smooth | Same |
| Ribs and Veins | Prominent | Same |
| Margins | Deeply indented | Same |
| Serration | Slightly to moderate | Same |
| Stipules | Rudimentary | Same |
| BLOOM: | | |
| Size | 8.89 cm | Same |
| Borne | Clusters on elongated pedicels | Same |
| Stem Strength | Strong | Same |
| Form | Decorative | Same |
| Color: | | |
| Center | 77a-77B | 74A |
| Upper side | 77B-77C | 76A-76B |
| Lower side | 77C-77D | 76C-76D |
| Tonality | orchid to light purple | Lavender to Orchid |
| PETALS: | | |
| Texture | Smooth | Same |
| Appearance | Open at base, broading quickly | Same |

-continued

TABLE OF COMPARISON

| | New Cultivar (Diana) | Dolly |
|---|---|---|
| and form | to wide flat keel tapering to a blunt point. | |
| Arrangement | Composite | Same |
| Persistance | Resists shattering | Same |
| Fragrance | Typical chrysanthemum | Same |
| REPRODUCTION ORGANS: | | |
| Stamen | 2 to 15 | Same |

-continued

TABLE OF COMPARISON

| | New Cultivar (Diana) | Dolly |
|---|---|---|
| Pollen | None to scant | Same |
| Arrangement | Custered in center of flower if present | Same |
| Styles | Present in both ray & disc florets | Same |
| Length | Short | Same |
| Ovaries | At base of petal attached to receptacle | Same |

We claim:

1. A new and distinctive cultivar of chrysanthemum plant, substantially as herein described, and distinguished from its parent by a darker flower color and increased "rolled" or "spoon shaped" petals.

* * * * *

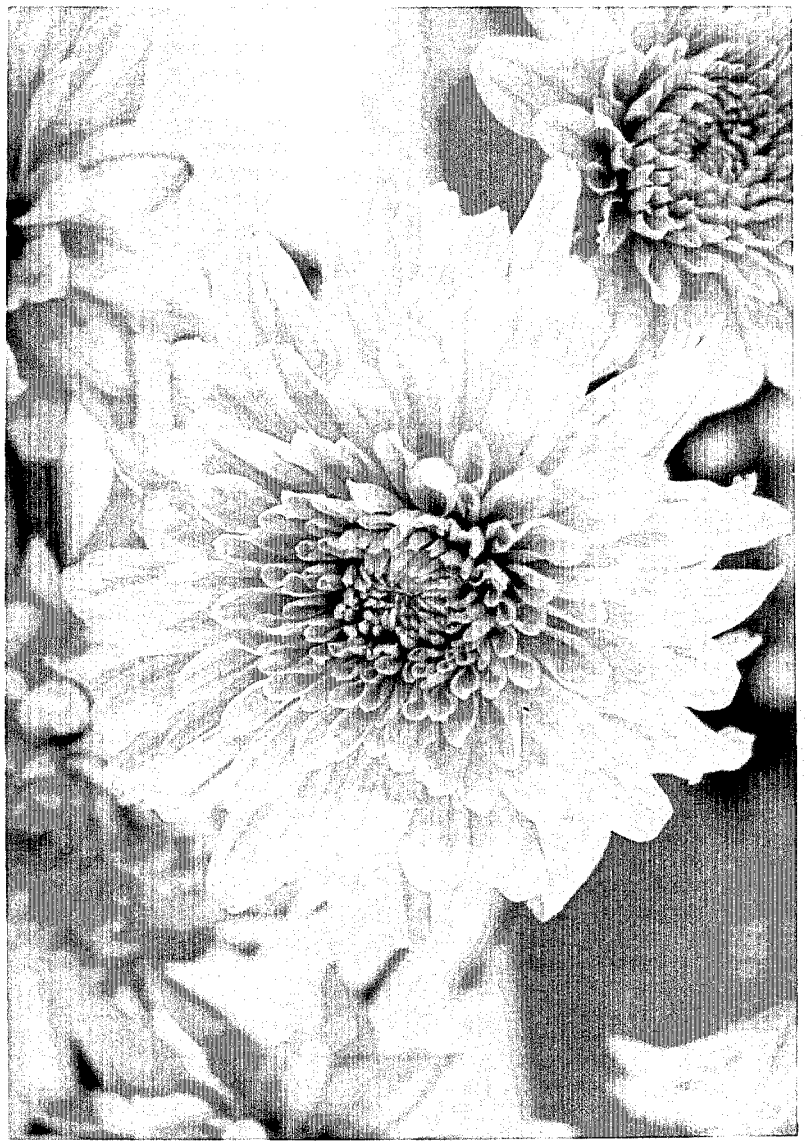

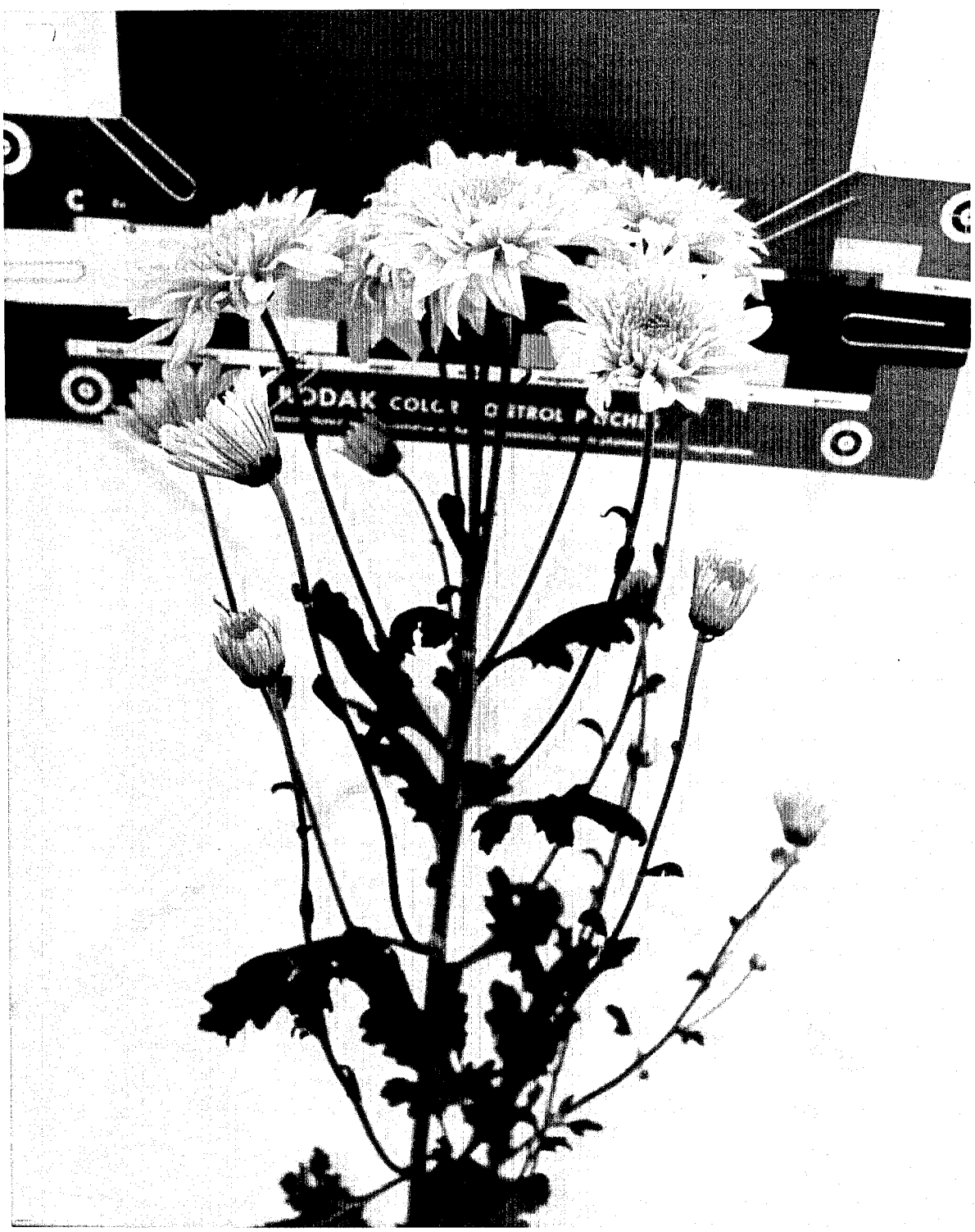
KODAK

UNITED STATES PATENT AND TRADEMARK OFFICE

CERTIFICATE OF CORRECTION

PATENT NO. : PP 5496

DATED : June 18, 1985

INVENTOR(S) : Margot J. Persoon and Johannes A. Persoon

It is certified that error appears in the above-identified patent and that said Letters Patent is hereby corrected as shown below:

The photograph depicting the overall form and appearance of the plant should be inserted as per attached sheet In column 1, line 47, delete "pO" before the word"Botanical".

In column 2, line 42, delete "77a" and insert ---77A---.

In column 1, after line 39, insert the following:

DETAILED DESCRIPTION OF THE DRAWING

The following is a detailed description of the new Chrysanthemum plant of the present invention. The color terminology used in the following is in accordance with the Royal Horticltural Society Colour Chart.

In column 2, line 28, the designation "136A" and "same" should be moved to line 29 after the words "Upper side".

On the title page, "1 Drawing Figure" should read --2 Drawing Figures--.

Signed and Sealed this

*Nineteenth* Day of *August 1986*

[SEAL]

*Attest:*

DONALD J. QUIGG

*Attesting Officer*

*Commissioner of Patents and Trademarks*